United States Patent
Cohen et al.

[11] Patent Number: 5,980,527
[45] Date of Patent: Nov. 9, 1999

[54] BONE CAVITY SEALING ASSEMBLY

[75] Inventors: Andrew Michael Cohen, Goole; John Naybour, Clwyd, both of United Kingdom

[73] Assignee: DePuy International, Leeds, United Kingdom

[21] Appl. No.: 08/978,990

[22] PCT Filed: May 23, 1996

[86] PCT No.: PCT/GB96/01241

§ 371 Date: May 1, 1998

§ 102(e) Date: May 1, 1998

[87] PCT Pub. No.: WO96/38104

PCT Pub. Date: Dec. 5, 1996

[30] Foreign Application Priority Data

May 30, 1995 [GB] United Kingdom ............ 9510917

[51] Int. Cl.⁶ .................................................. A61B 17/58
[52] U.S. Cl. ................................................ 606/92
[58] Field of Search ........................ 606/92, 93, 94, 606/95, 99, 86

[56] References Cited

U.S. PATENT DOCUMENTS

| | | |
|---|---|---|
| 4,031,569 | 6/1977 | Jacob . |
| 4,274,163 | 6/1981 | Malcom et al. . |
| 4,488,549 | 12/1984 | Lee et al. . |
| 4,815,454 | 3/1989 | Dozier, Jr. . |
| 4,997,448 | 3/1991 | Filer . |
| 5,047,061 | 9/1991 | Brown . |
| 5,429,143 | 7/1995 | Marzluff et al. . |

FOREIGN PATENT DOCUMENTS

| | | |
|---|---|---|
| 583975 | 8/1993 | European Pat. Off. . |
| WO/ 90/00375 | 7/1988 | WIPO . |

*Primary Examiner*—Michael Buiz
*Assistant Examiner*—(Jackie) Tan-Uyen T. Ho
*Attorney, Agent, or Firm*—Merchant & Gould P.C.

[57] ABSTRACT

A bone cavity sealing gasket which can be fitted over the resected end of a bone (2) to be provided with bone cement in its axial cavity, includes a sealing plate (10, 40) which has a quantity of a resiliently deformable material on its lower face to enable a seal to be created between the plate (10, 40) and the upper edge of the bone, and an opening (12, 42) extending through it. A plug (14, 30, 44) can be received in the opening (12,42) in the sealing plate (10, 40). The plug (14,30,44) has an injection port (26, 32) extending through it aligned with the opening (12, 42) in the sealing plate (10, 40) in which the injection nozzle (16) of bone cement delivery apparatus can be received.

14 Claims, 3 Drawing Sheets

BONE CAVITY SEALING ASSEMBLY

FIELD OF THE INVENTION

This invention relates to a bone cavity sealing gasket which can be fitted over the resected end of a bone to be provided with bone cement in its axial medullary cavity, to an assembly for injecting bone cement into a bone cavity which includes the bone cavity sealing gasket, and to a method of injecting bone cement into a bone cavity.

BACKGROUND OF THE INVENTION

The formation of cement bond between a bone and a prosthesis generally involves injection of bone cement into the cavity of the bone and location of the prosthesis in the cement in the cavity. The bond involves the cement grout interlocking with the bone and the prosthesis. Generally, the end of the bone will be resected before location of the prosthesis. This technique is used, for example, in hip, knee and shoulder replacement.

It is generally desirable to inject the cement into the cavity under pressure to ensure that the cavity is properly filled with cement. The application of pressure to the cement in the cavity requires that flow of the cement out of the cavity be controlled. It is known to control the flow of cement by means of a sealing gasket which can be fitted over the resected end of the bone, through which the bone cement can be injected into the bone cavity. Once the cement has been injected, the gasket is removed with or after removal of the cement injection apparatus allowing the prosthesis then to be located in the cement in the cavity.

Removal of the gasket after injection of the cement and before location of the prosthesis has the disadvantage that the injected cement can be disturbed, possibly weakening the bond of the cement to the bone cavity.

SUMMARY OF THE INVENTION

The present invention provides a bone cavity sealing gasket which comprises a sealing plate with an opening in it through which a prosthesis can be located in the bone cavity, and in which a plug can be received through which cement can be injected into the cavity.

Accordingly, in one aspect, the invention provides a bone cavity sealing gasket which can be fitted over the resected end of a bone to be provided with bone cement in its axial cavity, the gasket comprising (a) a sealing plate which has a quantity of a resiliently deformable material on its lower face to enable a seal to be created between the plate and the upper edge of the bone, and an opening extending through it, and (b) a plug which can be received in the opening in the sealing plate and which has an injection port extending through it and through the opening in the sealing plate, in which the injection nozzle of bone cement delivery apparatus can be received.

The gasket of the invention has the advantage that it the sealing plate can remain in place on the resected end of the bone after injection of bone cement into the bone cavity and while the prosthesis is located in the cavity. In this way, the injected bone cement remains substantially undisturbed between injection and location of the prosthesis; in particular, it is not subjected to reduction of pressure and withdrawal of bone cement from trabecular spaces, which can arise when a sealing gasket is removed before the cement is sufficiently hardened. This means that the bond of the cement to the bone of the cavity can be established with greater confidence.

The sealing plate has a quantity of resiliently deformable material on its lower face which facilitates the formation of the seal to the bone. The deformable material enables deviations from planarity in the end face of the bone to be accommodated without disrupting the seal unacceptably. The deformable material might be for example a material with elastomeric properties. An example of a suitable material might be a silicone based material. The material will be provided in the region of the sealing plate in sufficient thickness to enable a sufficient seal to be made to the bone, taking into account the deviations from planarity of the end of the bone and the force that can be applied to the sealing plate against the bone. For example, the deformable material might be provided with a thickness of at least about 4 mm, preferably at least about 6 mm, especially at least about 10 mm. Generally, the material provided to form the seal to the bone will be provided preferentially in edge regions of the sealing plate as a border for the sealing plate of sufficiently width to accommodate the range of bones on which the gasket is to be used. The provision of sealing material in a border around the sealing plate has the advantage that the plate can remain sufficiently flexible to be capable of being deformed to accommodate variations in the configuration of the resected end of the bone. When provided as a border, the width of the border might be, for example, at least about 6 mm, preferably at least about 8 mm, for example at least about 10 mm. Preferably, the width is not more than about 20 mm, more preferably not more than about 15 mm.

The deformable material will be selected so that it is sufficiently resiliently deformable to form an appropriate seal to the bone under the force that can be applied to the sealing plate against the bone.

The sealing plate can suitably have a generally planar upper surface, although this is not essential.

The sealing plate can have a lip formed on its lower surface extending around the plate to engage the outer edge of the bone when the sealing plate is forced against the bone. The lower surface will then be non-planar and the seal between the plate and the bone will be line contact rather than surface to surface contact. This can facilitate formation of an effective seal. Preferably, the lip has an inclined surface for engaging the bone, so that a number of different bone sizes and configurations can be accommodated.

The sealing gasket can include a flap portion which can be used to control flow of bone cement from one or more other openings into the bone cavity. Such a sealing gasket might be used for example on a femur whose trochanter has been resected. For example, the sealing plate can be provided with a sealing flap portion extending at an angle relative to the plate, to extend over the resected trochanter and to control egress of bone cement from the trochanter region and to apply pressure to that cement. The angle might be in the range of from about 65° to about 120°. The precise angle will depend on the configuration of the bone to which the gasket is to be fitted. The formation of the flap portion on a sealing gasket made from flexible material allows the orientation of the flap to be adjusted to suit particular applications.

The sealing plate can be formed of one material which provides the seal between the plate and the bone around the edges of the plate, and the portion of the sealing plate extending between the edges. Such a sealing plate can conveniently be formed in a single moulding step from the resiliently deformable material which provides the seal. The use of the resiliently deformable material to provide that portion of the sealing plate which extends between the edges has the advantage that the plate as a whole can be made flexible so as better to accommodate deviations from planarity of the edges of the bone to which the seal is to be made.

Other constructions of sealing plate can be used. For example, different materials might be used for the edge regions where the seal is to be formed to the bone, and that portion of the sealing plate which extends between the edge regions.

The sealing plate and the plug will generally be arranged so that a seal can be formed between them, to minimise leakage of bone cement from the bone cavity through the opening in the sealing plate, around the plug inserted therein. An appropriate seal can suitably be created by forming one or both of the plug and the sealing plate (at least around the opening) from a resiliently deformable material. It can be preferred for some applications for the plug at least to be made at least partially from such a material since that can facilitate the formation of seals between the plug and one or both of the sealing plate and the injection nozzle of the bone cement delivery apparatus.

It can be preferred for the plug and sealing plate to be formed from the same material.

The plug can have at least one laterally extending lug or, for some applications a plurality of laterally extending lugs (which can extend all or just part of the way around the periphery of the plug), towards the end which protrudes from the opening in the sealing plate, which engage the underside of the sealing plate around the opening to retain the plug in the opening. When the lug extends all or substantially all of the way around the plug, it can be in the form of a flange. The lug or lugs can be formed from a resiliently deformable material which can facilitates engagement of the plug with the opening in the sealing plate, and subsequent removal of the plug, by deformation of the lugs. The lug or lugs can be appropriately profiled at their edge or edges to facilitate insertion into the opening in the sealing plate and deformation of the plate, for example by an appropriate taper at the edge(s).

It is also envisaged that the lug or lugs on the plug can be formed from a relatively rigid material so that, when the plug is inserted into the opening in the sealing plate and the sealing plate is made from a deformable material, the engagement of the plug with the opening and the subsequent removal of the plug are facilitated by deformation of the sealing plate. An advantage of the use of a rigid lug on the plug is that its lateral extent can be kept small without compromising the ability of the lug to retain the plug in the opening. This can facilitate the insertion of the plug into the opening.

The body of the plug and the lug or lugs provided on it can be formed from the same material, for example from a relatively rigid material. This has the advantage that the plug does not flex when force is applied to it, for example by means of an inserted injection nozzle.

The plug can have a back plate which rests on the top surface of the sealing plate when the plug is inserted into the opening in the plate. The back plate can be used to manipulate the plug. The back plate can have a planar lower surface. It might then be used to apply pressure to the sealing plate to form the seal between the plate and the upper edge of the bone, particularly when the back plate (and possibly the entire plug) is formed from a material that is more rigid than that of the sealing plate.

In another aspect, the invention provides a method of locating a prosthesis in the cavity of a resected bone, which comprises:

(a) locating a bone cavity sealing gasket of the type discussed above so that the sealing plate is located on the resected edge of the bone, (b) applying pressure to the sealing plate to force it against the said resected edge to form a seal between the sealing plate and the bone, (c) injecting bone cement into the bone cavity by means of bone cement delivery apparatus having an injection nozzle received in the injection port in the plug of the gasket, (d) removing the bone cement delivery apparatus and the plug from the sealing gasket, and (e) inserting a prosthesis into the bone cavity, through the opening in the sealing plate.

The method will generally include the step of removing the sealing plate from the end of the bone. Preferably, the sealing plate is severed before being removed so that it can be removed by lateral movement relative to the prosthesis rather than having to be drawn over the prosthesis towards its free end.

In a further aspect, the invention provides an assembly for injecting bone cement into a bone cavity, which includes a bone cavity sealing gasket of the type discussed above. The assembly can include bone cement delivery apparatus including a nozzle which can be received in the injection port in the plug so as to form a seal in the plug; the seal can be substantially complete so as to restrict the flow of bone cement from the bone cavity substantially completely, or it can be partial so as to restrict that flow partially. The assembly can include a tool for applying force to the sealing gasket around the opening, to force the sealing plate against the upper edge of the bone. Preferably, the tool has limbs which can extend around at least a substantial part of the opening in the sealing plate; for example, the tool might be substantially u-shaped so that it can be positioned on the sealing plate (and subsequently removed) by a lateral sliding movement and engage the sealing plate along three edges thereof. The assembly can include a prosthesis to be fitted into the bone cavity which can be located in the bone cavity by insertion through the opening in the sealing plate after removal from the opening of the plug.

BRIEF DESCRIPTION OF THE DRAWINGS

The present invention will now be described, by way of example only, with reference to the accompanying drawings, in which.

DETAILED DESCRIPTION OF PREFERRED EMBODIMENTS

Figure 1:
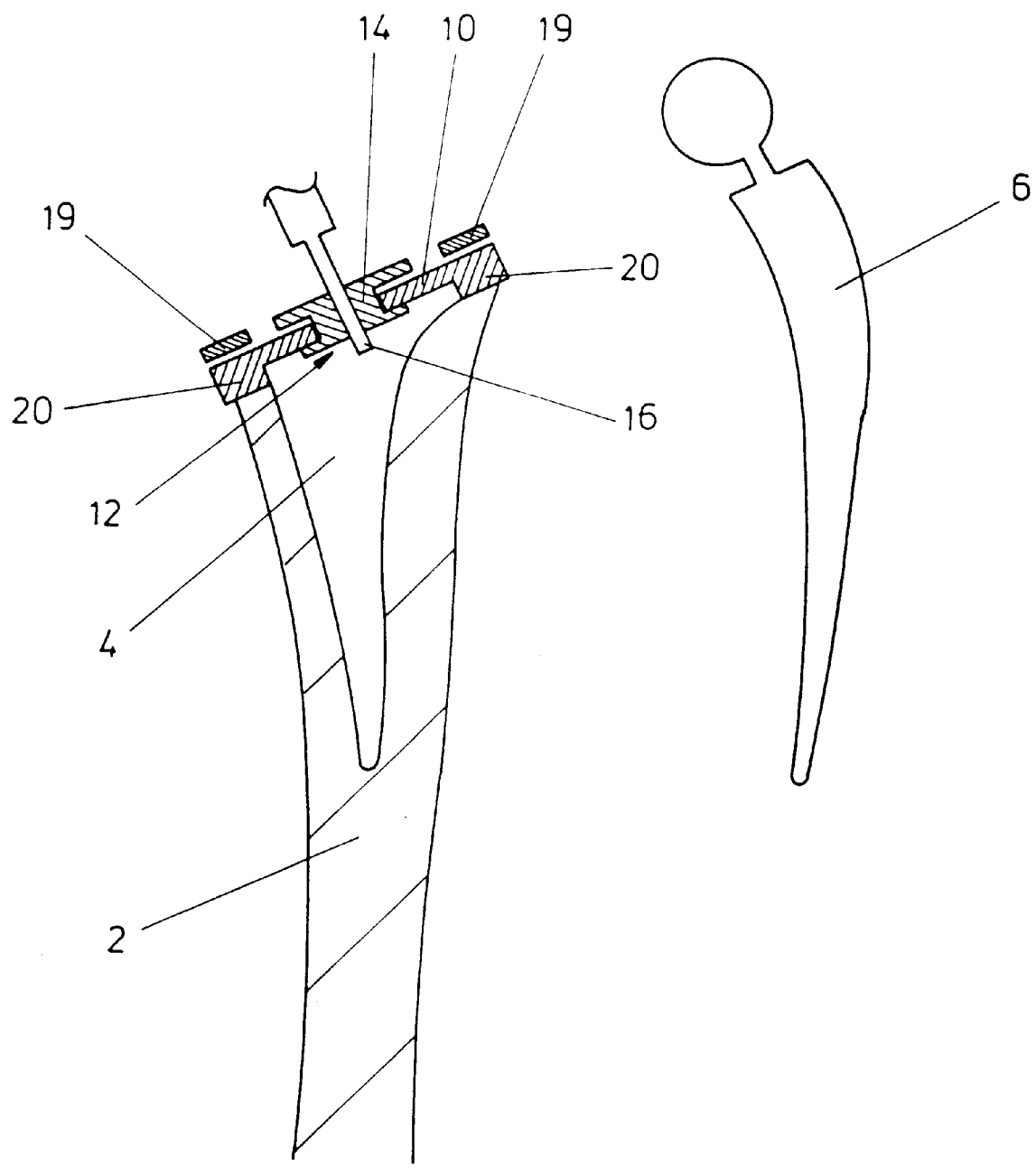
FIG. 1 is a sectional elevation through the upper end portion of a femur which has been resected and which has a sealing gasket according to the invention on its upper end.

Referring to the drawings, FIG. 1 shows a femur 2 which has been resected at its upper end. Cancellous bone has been removed from the centre of the femur at the upper end to form a cavity 4 in which a prosthesis 6 is to be located. The prosthesis comprises a stem which is received in the cavity and a head which engages an acetabular cup component, as is known.

The stem of the prosthesis is bonded to the bone of the cavity by means of bone cement injected into the cavity under pressure. Pressure in the cement injected into the cavity is maintained during and after injection (while the cement hardens) by means of a sealing gasket positioned over the end of the bone. The gasket comprises a sealing plate 10 having an opening 12 in it, and a plug 14 located in the opening in which the nozzle 16 of bone cement delivery apparatus can be received.

Force can be applied to the gasket against the bone directly, or by means of a u-shaped tool 19 which can be located around the opening 12 in the sealing plate.

Figure 2:
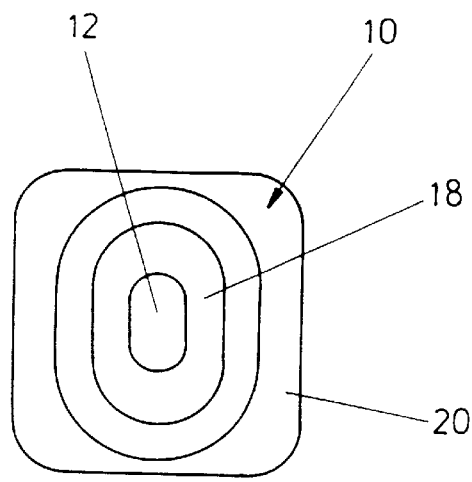
FIG. 2 is a view from below of the sealing plate of the sealing gasket shown in FIG. 1.
Figure 3:
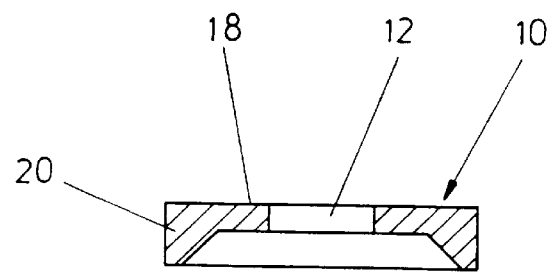
FIG. 3 is a sectional elevation through the sealing plate shown in FIG. 2.

Referring to FIGS. 2 and 3, the sealing plate is formed from a resiliently deformable material such as a silicone by moulding. It has a thin central portion 18 surrounding the opening 12 and a relatively thick edge portion 20 defining a lip. The lip has an inclined under-surface for engaging the upper edge of the resected bone in line contact. For example, the thickness of the plate in the portion surrounding the opening might be about 7 mm and the thickness at the edge might be about 12 mm. The width of the edge portion is about 10 mm at its widest along the long edges of the sealing plate and about 5 mm at its narrowest along the short edges of the sealing plate.

The dimensions of the sealing plate will be selected according to the bone against which it is to be used and the prosthesis which is to be inserted into the bone cavity. For example, a sealing plate to be used against the femur of an adult human might have dimensions 60 mm by 55 mm. The opening in the plate has dimensions 20 mm by 11 mm.

The opening 12 in the sealing plate is generally oval, having semi-circular portions at each end joined by straight portions.

Figure 4:
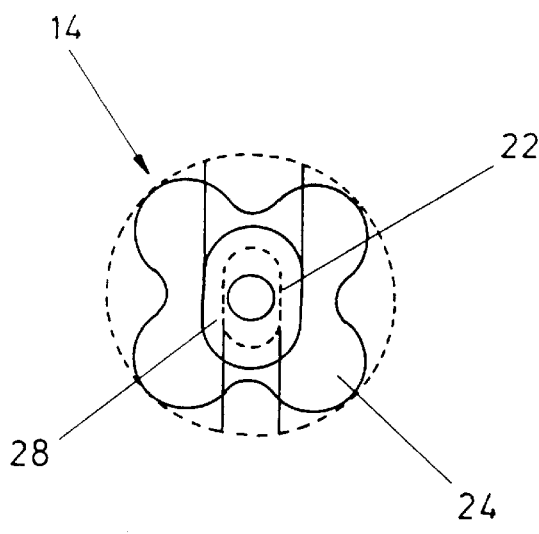
FIG. 4 is a view from below of the plug of the sealing gasket shown in FIG. 1.
Figure 5:
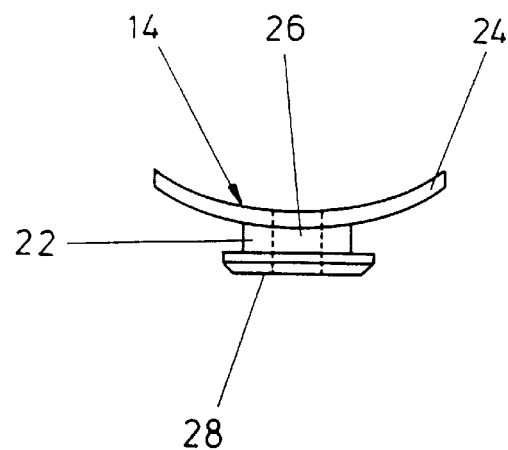
FIG. 5 is a sectional elevation through the plug shown in FIG. 4.

Referring to FIGS. 4 and 5, the plug 14 is formed from a resiliently deformable material by moulding. It can be formed from the same material as that of the sealing plate, although a material that is more rigid than that of the sealing plate can be preferred for some applications. It comprises a neck portion 22 which is generally oval in cross-section with a shape corresponding substantially to that of the opening 12 in the sealing plate 10. There is a back plate 24 on the neck, by which the plug can be gripped and manipulated, in particular during insertion into and removal from the opening 12 in the sealing plate. The back plate can be curved upwardly as shown in FIG. 5 to facilitate manipulation of the plug.

An injection port 26 extends through the plug, in which the nozzle of bone cement delivery apparatus can be received.

A laterally extending lug 28 in the manner of a flange depends from the lower end of the neck portion 22, which can engage the lower face of the sealing plate when the plug is located in the opening 12, restricting inadvertent removal of the plug from the opening. The lug has a profiled lower edge to facilitate insertion into the opening in the sealing plate.

Figure 6:
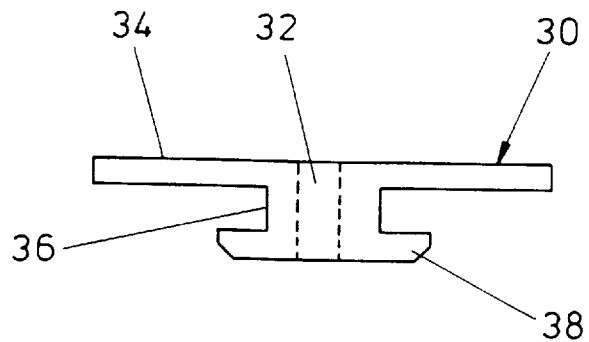
FIG. 6 is a sectional elevation of further embodiment of plug for use in a sealing gasket according to the invention.

FIG. 6 shows a plug 30 for use in the sealing plate of a sealing gasket, such as described above with reference to FIGS. 2 and 3. The plug has a neck portion 36 and a flange-like lug 38 which extends around its periphery. An injection port 32 extends through the plug, in which the nozzle of bone cement delivery apparatus can be received. The plug 30 is made from a relatively rigid material so that, on insertion into the opening in a sealing plate, the material of the sealing plate is deformed by the lug 38.

The plug has a back plate 34 which is flat. A plug with a flat back plate formed from a rigid material can be used to apply pressure to the sealing plate, to form the seal between the plate and the bone.

Figure 7:
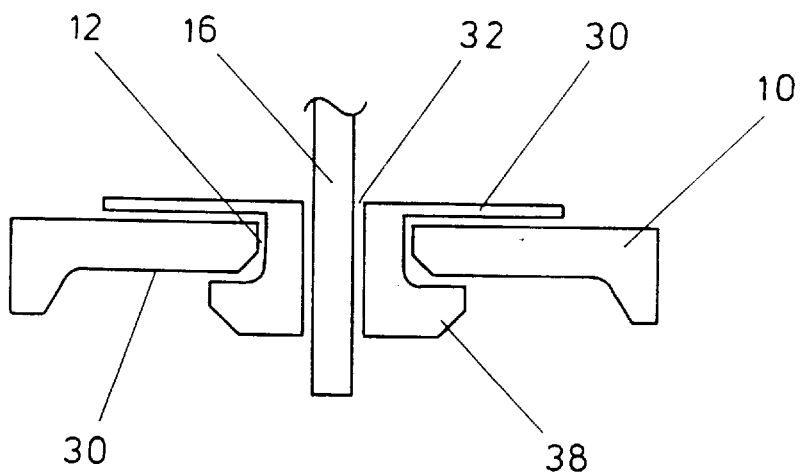
FIG. 7 is a sectional elevation through a sealing gasket according to the invention, with the nozzle of bone cement delivery apparatus inserted into the injection port in the plug.

FIG. 7 shows the plug 30 located in the opening 12 in the sealing plate 10 with the neck portion of the plug engaging the edges of the opening. The lug 38 extends laterally in contact with the lower face 30 of the sealing plate, restricting removal of the plug from the opening. The nozzle 16 of bone cement delivery apparatus is received in the injection port 32 which extends through the plug, for delivery of cement through the sealing gasket into the cavity of a bone against which the gasket is positioned in use.

In use, after injection of bone cement into the bone cavity, the plug 30 is removed from the opening 12 in the sealing plate 10. The plug can be removed soon after injection of the cement. However, it can be preferred for its removal to be deferred until the cement has partially hardened, for example, until it has hardened sufficiently for insertion into the cavity of the prosthesis. The prosthesis to be located in the bone cavity can be inserted in the cavity through the opening 12 after removal of the plug.

Once the bone cement has hardened sufficiently to bond the prosthesis to the bone, the sealing plate can be removed from the bone. Preferably, the sealing plate is severed before removal, for example by tearing or more preferably by cutting, from the opening 12 to an edge of the plate, so that it can be removed by lateral movement rather than having to be passed over the end of the prosthesis.

Figure 8:
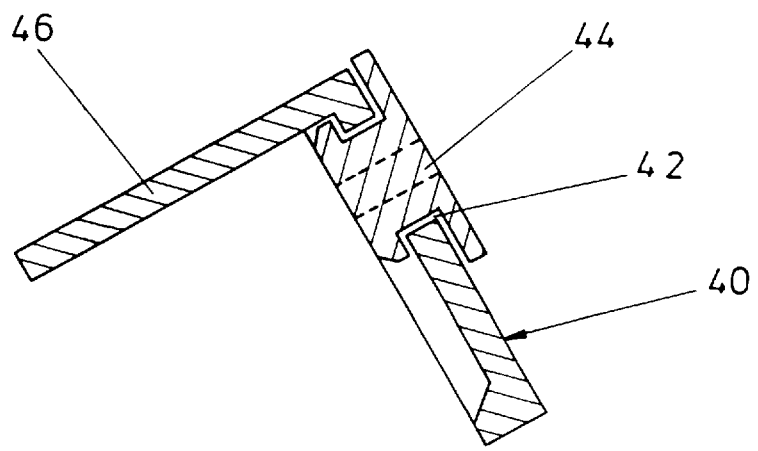
FIG. 8 is a sectional elevation through a sealing gasket according to the invention, which includes a flap portion to control flow of bone cement from a bone cavity which has been resected across two planes.

FIG. 8 shows a sealing gasket in which the sealing plate 40 has an opening 42 in it to accommodate a plug 44, generally as described above in relation to other embodiments. The sealing plate also has a flap portion 46 extending from the portion with the opening 42 in it, which can be used to pressurise and to control flow of bone cement from an opening into the bone cavity other than the opening into which cement is to be injected through the opening in the sealing plate and the plug inserted therein. For example, it can be used to extend over the resected trochanter on a femur, and to control egress of bone cement from the trochanter region and to apply pressure to that cement.

The sealing gasket of the invention has the advantage that the component by which cement is retained in place in the bone cavity does not need to be moved from the end of the bone throughout the period from injection of bone cement to hardening of the cement to form the bond between the bone and the prosthesis located in the cement in the cavity. This allows pressure to be maintained on the cement throughout the period in which it hardens, as preferred for secure bonding of the cement to the bone.

While the invention has been described with reference to the drawings as applied to a hip joint, it will be understood that the invention is applicable to other joints.

We claim:

1. A bone cavity sealing gasket which can be fitted over the resected end of a bone to be provided with bone cement in its axial cavity, the gasket comprising:
   (a) a sealing plate which can be fitted over the resected end of the bone and has a quantity of a resiliently deformable material on its lower face to enable a seal to be created between the plate and the upper edge of the bone, and
   (b) a plug which has an injection port extending through it in which the injection nozzle of bone cement delivery apparatus can be received, the sealing plate having an opening extending through it (i) in which the plug which can be received for injection of bone cement from the delivery apparatus into the bone cavity, and (ii) through which a prosthesis which is to be bonded to the bone of the cavity by the bone cement can be inserted into the cavity after injection of the cement and removal of the plug.

2. A bone cavity sealing gasket as claimed in claim 1, in which the sealing plate is formed from the said resiliently deformable material by moulding.

3. A bone cavity sealing gasket as claimed in claim 1, or claim 2, in which the plug is formed from a resiliently deformable material.

4. A bone cavity sealing gasket as claimed in claim 1, in which the plug is formed from a relatively rigid material which is received in the opening in the sealing gasket by deformation of the sealing gasket around the opening therein.

5. A bone cavity sealing gasket as claimed in claim 1, in which the plug has at least one laterally extending lug towards the end which protrudes from the opening in the sealing plate, which engages the underside of the sealing plate around the opening to retain the plug in the opening.

6. A bone cavity sealing gasket as claimed in claim 1, which includes a flap portion for controlling flow of bone cement from an opening into the bone cavity other than the opening into which cement is to be injected through the opening in the sealing plate and the plug inserted therein.

7. A bone cavity sealing gasket as claimed in claim 6, in which the flap portion is provided on the sealing plate.

8. An assembly for injecting bone cement into a bone cavity, which comprises a bone cavity sealing gasket as claimed in claim 1, and bone cement delivery apparatus which includes a nozzle which can be received in the injection port in the plug so as to form seal in the plug.

9. An assembly for injecting bone cement into a bone cavity, which comprises a bone cavity sealing gasket as claimed in claim 1, and a tool for applying force to the sealing gasket around the opening, to force the sealing plate against the upper edge of the bone.

10. An assembly as claimed in claim 9, in which the tool has limbs which can extend around at least a substantial part of the opening in the sealing plate.

11. An assembly for injecting bone cement into a bone cavity, which comprises a bone cavity sealing gasket as claimed in claim 1, and a prosthesis to be fitted into the bone cavity which can be located in the bone cavity by insertion through the opening in the sealing plate after removal from the opening of the plug.

12. A method of locating a prosthesis in the cavity of a resected bone, which comprises:
   (a) locating a bone cavity sealing gasket as claimed in claim 1 so that the sealing plate is located on the resected edge of the bone,
   (b) applying pressure to the sealing plate to force it against the said resected edge to form a seal between the sealing plate and the bone,
   (c) injecting bone cement into the bone cavity by means of bone cement delivery apparatus having an injection nozzle received in the injection port in the plug of the gasket,
   (d) removing the bone cement delivery apparatus and the plug from the sealing gasket, and
   (e) inserting a prosthesis into the bone cavity, through the opening in the sealing plate.

13. A method as claimed in claim 12, which includes the step of removing the sealing plate from the end of the bone.

14. A method as claimed in claim 13, in which the sealing plate is severed before being removed, so that it can be removed by lateral movement relative to the prosthesis.

* * * * *